US010689688B2

(12) United States Patent
Lowe

(10) Patent No.: US 10,689,688 B2
(45) Date of Patent: Jun. 23, 2020

(54) DETECTING CHEMICAL AND BIOLOGICAL AGENTS USING TEXTILE-BASED SENSORS

(71) Applicant: SRC, Inc., North Syracuse, NY (US)

(72) Inventor: Adam J. Lowe, Syracuse, NY (US)

(73) Assignee: SRC, Inc., North Syracuse, NY (US)

( * ) Notice: Subject to any disclaimer, the term of this patent is extended or adjusted under 35 U.S.C. 154(b) by 0 days.

(21) Appl. No.: 15/973,694

(22) Filed: May 8, 2018

(65) Prior Publication Data

US 2018/0251823 A1 Sep. 6, 2018

Related U.S. Application Data

(62) Division of application No. 13/629,846, filed on Sep. 28, 2012, now Pat. No. 9,982,292.

(51) Int. Cl.

| | |
|---|---|
| ***G01N 33/543*** | (2006.01) |
| ***C12Q 1/6825*** | (2018.01) |
| *C12Q 1/6823* | (2018.01) |
| *C12Q 1/6804* | (2018.01) |

(52) U.S. Cl.

CPC ......... *C12Q 1/6825* (2013.01); *G01N 33/543* (2013.01); *G01N 33/54346* (2013.01); *C12Q 1/6804* (2013.01); *C12Q 1/6823* (2013.01)

(58) Field of Classification Search

CPC ............ G01N 33/54346; C12Q 1/6804; C12Q 1/6823; C12Q 1/6825

See application file for complete search history.

(56) References Cited

U.S. PATENT DOCUMENTS

| | | | | |
|---|---|---|---|---|
| 5,955,268 A * | 9/1999 | Granados | C12Q 1/6825 | 435/194 |
| 6,221,579 B1 * | 4/2001 | Everhart | G01N 21/4788 | 435/287.2 |
| 7,892,734 B2 * | 2/2011 | Lu | C12Q 1/6818 | 435/6.11 |
| 2001/0054495 A1 * | 12/2001 | Yevin | F28D 15/02 | 165/104.26 |
| 2002/0137232 A1 * | 9/2002 | Nakamura | G01N 33/525 | 436/525 |
| 2003/0099940 A1 * | 5/2003 | Empedocles | B82Y 15/00 | 435/6.12 |
| 2006/0014172 A1 * | 1/2006 | Muller | B82Y 5/00 | 435/6.11 |
| 2009/0221080 A1 * | 9/2009 | Tajima | B01L 3/0275 | 436/43 |
| 2010/0304387 A1 * | 12/2010 | Jenison | C12Q 1/682 | 435/5 |

(Continued)

*Primary Examiner* — Christopher L Chin

(74) *Attorney, Agent, or Firm* — Bond Schoeneck & King, PLLC

(57) ABSTRACT

Methods and systems for detecting chemical and biological agents using oligonucleotide aptamers. A sensor includes a detection aptamer that has a binding domain for the chemical or biological agent, and is bound to fibers of a textile such as a patch or article of clothing. The detection aptamer can be stabilized and enhanced through a stabilization agent such as trehalose or through binding to a nanoparticle which is then bound to the fiber. Binding of the chemical and biological agent of interest to the detection aptamer can be reported to the user or wearer of the textile in a variety of ways, including visually and electrically.

14 Claims, 5 Drawing Sheets

500 220 510 210 410

(56) References Cited

U.S. PATENT DOCUMENTS

2012/0058697 A1* 3/2012 Strickland .............. B82Y 15/00
442/59
2012/0322049 A1* 12/2012 Lowe ..................... C12Q 1/708
435/5
2013/0123137 A1* 5/2013 Reichardt .......... G01N 33/5008
506/9

* cited by examiner

DETECTING CHEMICAL AND BIOLOGICAL AGENTS USING TEXTILE-BASED SENSORS

RELATED APPLICATION DATA

This application is a divisional of U.S. patent application Ser. No. 13/629,846 filed Sep. 28, 2012, and entitled "Detecting Chemical And Biological Agents Using Textile-Based Sensors," now allowed, the entirety of which is incorporated by reference herein.

BACKGROUND OF THE INVENTION

1. Field of the Invention

The present invention relates to detection of chemical and biological agents and, more specifically, to detection of chemical and biological agents using textile-based sensors.

2. Description of the Related Art

There is an increasing demand for assays for the detection and quantitative identification of chemical and biological hazards across a broad range of disciplines, including food safety, homeland security, and medical diagnostics. While there is existing technology for the detection and quantitative identification of chemical and biological hazards, these sensors are generally large, bulky, and/or slow sensor systems that require considerable time and effort to utilize or to move from one location to another. Accordingly, there is a continued need for fast, efficient, and portable sensor systems for chemical and biological hazard detection.

Aptamers are single-stranded oligonucleic acid or peptide molecules that bind to a specific target molecule. The target molecule can be, for example, a protein, nucleic acid, cell, or tissue, among many others. While some aptamers are naturally occurring, most are designed for a specific target. Due to the high affinity and specificity for their target(s) of interest, aptamers are increasingly used as diagnostic reagents. Accordingly, aptamers are a potential component of sensors for the detection and quantitative identification of chemical and biological hazards.

BRIEF SUMMARY OF THE INVENTION

It is therefore a principal object and advantage of the present invention to provide a method, device, and/or system for the detection of chemical and biological hazards.

It is another object and advantage of the present invention to provide a method, device, and/or system that utilizes aptamer technology to detect chemical and biological hazards.

It is yet another object and advantage of the present invention to provide a wearable, aptamer-based sensor for the detection of chemical and biological hazards.

Other objects and advantages of the present invention will in part be obvious, and in part appear hereinafter.

Embodiments include systems and methods for detecting chemical and biological agents using oligonucleotide aptamers. A textile-based sensor for detecting the presence of a biological or chemical target comprises: (i) a plurality of textile fibers; and (ii) a plurality of aptamer molecules each comprising a target binding domain and immobilized to the plurality of textile fibers, wherein, in the presence of the target, the target binds to the target binding domain of one or more of the plurality of aptamer molecules and a reporter signal is generated by the sensor. The sensor can further comprise a stabilizing agent such a trehalose, and a first and/or second plurality of nanoparticles for stabilization and/or detection.

A further embodiment comprises a textile-based sensor for detecting the presence of a biological or chemical target comprising: (i) a plurality of textile fibers; (ii) a plurality of aptamer molecules, each comprising a target binding domain, immobilized to the plurality of textile fibers; (iii) a plurality of nanoparticles immobilized to a terminal end of the aptamer molecules; and (iv) a stabilizing agent adapted to stabilize the plurality of aptamer molecules; wherein, in the presence of the target, the target binds to the target binding domain of one or more of the plurality of aptamer molecules and one or more of the plurality of nanoparticles are released.

Another embodiment comprises a textile-based sensor for detecting the presence of a biological or chemical target comprising: (i) a plurality of textile fibers; (ii) a plurality of metal nanoparticles immobilized to the plurality of textile fibers; (iii) a plurality of aptamer molecules, each comprising a target binding domain, immobilized to the plurality of metal nanoparticles; (iv) a plurality of insulating nanoparticles immobilized to a terminal end of the aptamer molecules; and (v) a stabilizing agent adapted to stabilize the plurality of aptamer molecules, wherein, in the presence of the target, the target binds to the target binding domain of one or more of the plurality of aptamer molecules and one or more of the plurality of insulating nanoparticles are released, resulting in a change in an electrical characteristic of the sensor.

A further embodiment comprises a method for detecting the presence of a biological or chemical target using a textile-based sensor. According to one embodiment the method comprising the steps of: (i) contacting a sample with a sensor comprising a plurality of textile fibers and a plurality of aptamer molecules, each comprising a target binding domain, immobilized to the plurality of textile fibers, wherein in the presence of the target, said target binds to the target binding domain of one or more of the plurality of aptamer molecules; and (ii) detecting a reporter signal generated by the sensor in response to the target binding to the target binding domain of one or more of the plurality of aptamer molecules. The sensor can further comprise a stabilizing agent such a trehalose, and a first and/or second plurality of nanoparticles for stabilization and/or detection.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
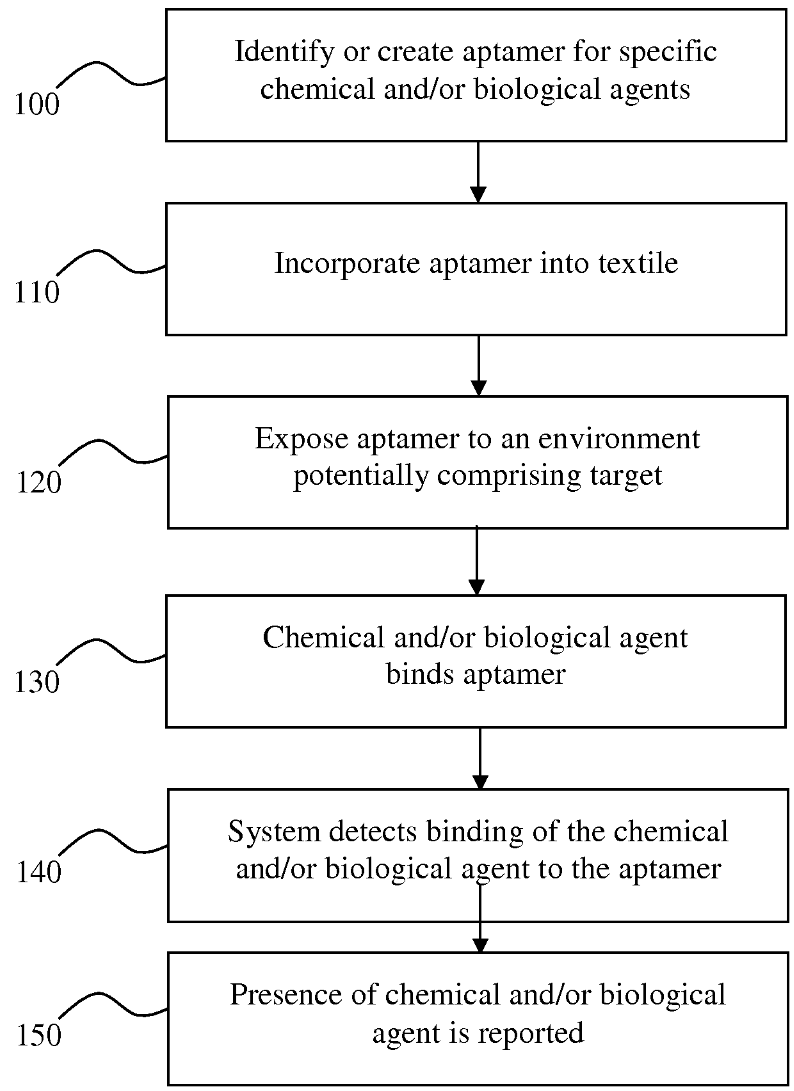
FIG. 1 is a flowchart of an exemplary process for detecting the presence of a chemical or biological agent using an aptamer in accordance with an embodiment of the present invention.

Referring now to the drawings wherein like reference numerals designate identical or corresponding parts or steps throughout the several views, there is shown in FIG. 1 a flowchart of an exemplary process for detecting the presence of a chemical or biological agent using aptamers. As an initial step 100, an aptamer with high specific affinity for a chemical or biological agent of interest is isolated, identified, or created. Examples of biological agents of interest which can be used as a biological weapon include numerous bacterium, virus, prion, and fungus varieties, as well as biological toxins, cells, or tissues. Examples of chemical agents of interest include mustard gas, chloride gas, and sarin, among many other examples. Some of the prime targets for detection by the present system include microorganisms such as *Bacillus anthracis*, members of the genii *Burkholderia, Rickettsia, Shingella, Vibrio*, and *Yersinia pestis*, viruses such as the smallpox virus, and toxic proteins such as ricin (from *Ricinus communis*) and botulinum toxin (from *Clostridum botulinum*), among many other agents.

The aptamer can be any nucleic acid or peptide suitable of binding to a chemical or biological agent targeted by the system. Aptamers comprising nucleic acid, typically DNA or RNA, usually consist of a short oligonucleotide polymer, while peptide aptamers usually consist of a short peptide domain and are often attached to a protein scaffold.

The aptamer can be created using any of a number of known methods in the art for isolating, identifying, or creating aptamers. While some aptamers are known to occur in nature, there are multiple methods used to selectively identify and create aptamers with high specific affinity for a target ligand such as a chemical or biological agent. The SELEX (systematic evolution of ligands by exponential enrichment) method, for example, uses multiple rounds of in vitro selection to selective—and then selectively evolve—a suitable aptamer from a large library of randomly generated oligonucleotide sequences.

At step 110 of the method depicted in FIG. 1, the anti-biological or chemical agent aptamer is incorporated into a textile carrier for deployment within an environment where the biological or chemical target may be present. In a preferred embodiment, the anti-biological or chemical agent aptamer is covalently attached to a portion of the textile carrier. The term "textile" as used herein refers to any fiber, filament, or other structural component of fabric, cloth, or clothing worn or carried by an individual.

Figure 2:
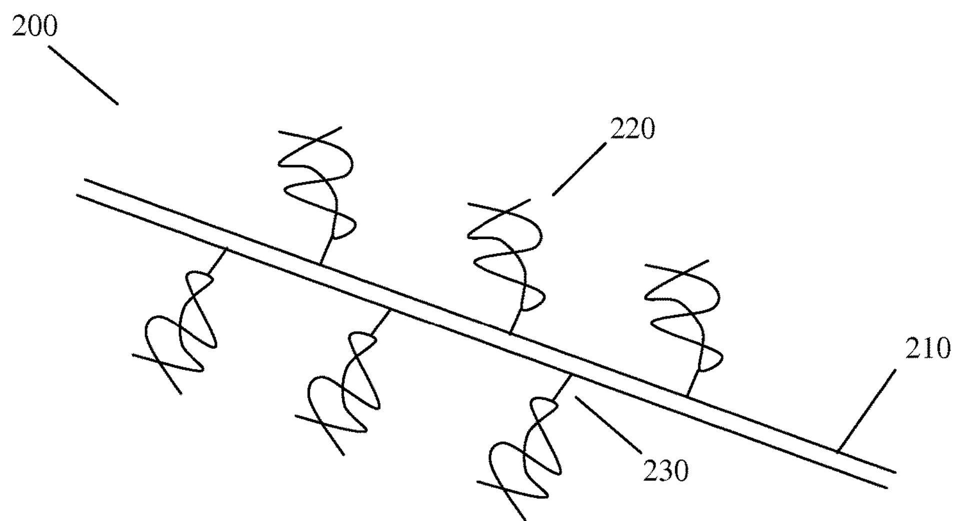
FIG. 2 is a schematic representation of a system for detecting the presence of a chemical or biological agent using an aptamer in accordance with an embodiment of the present invention.

FIG. 2 depicts a system 200 comprising a textile fiber 210, which can be a natural fiber, a synthetic fiber, or a combination of the two, and a plurality of aptamers 220 which are bound to the fiber, optionally through use of a linker 230 which can be a portion of the aptamer or a component of the system other than the aptamer. Examples of natural fibers include cotton, wool, silk, and linen, among others. Examples of synthetic fibers include nylon, polyester, polyethylene, polypropylene, vinyl, rayon, and a wide variety of other synthetic fibers.

Figure 3:
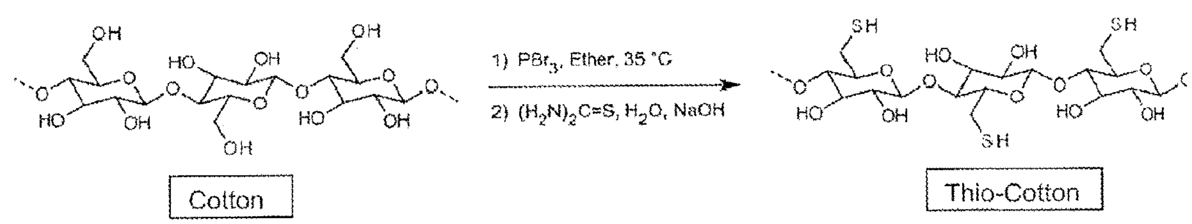
FIG. 3 is a schematic representation of a system for binding an aptamer to a textile in accordance with an embodiment of the present invention.

The aptamer can be attached to textile fiber 210 through a variety of mechanisms. One such mechanism is thiolation as shown in FIG. 3; the fiber and the aptamers can be thiolated using one of a number of chemical processes known in the art, and the thiolated apaters can be attached directly to the cotton through the thiol groups. Similarly the primary alcohol can be converted to a carboxy group through potassium permanganate when could then be used to add aminated oligonucleotides through EDC-NHS chemistry. Other mechanisms of attaching the aptamer to the textile fiber are possible.

It may also be beneficial to stabilize the aptamers and/or the fibers to promote a more stable system 400, and to enable the aptamers to function when out of solution. For example, system 400 could be stabilized with trehalose molecules 410, a naturally-occurring disaccharide formed from two $\alpha$-glucose units. As another example, the system could be stabilized with a hydrogel or other polymer (natural or synthetic).

Figure 4:
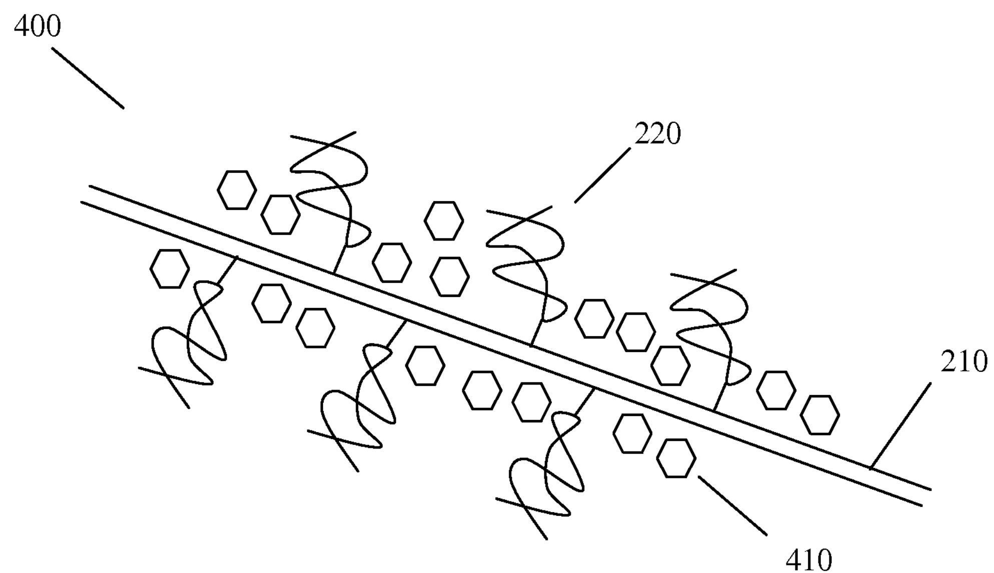
FIG. 4 is a schematic representation of a system for detecting the presence of a chemical or biological agent using an aptamer in accordance with an embodiment of the present invention.
Figure 5:
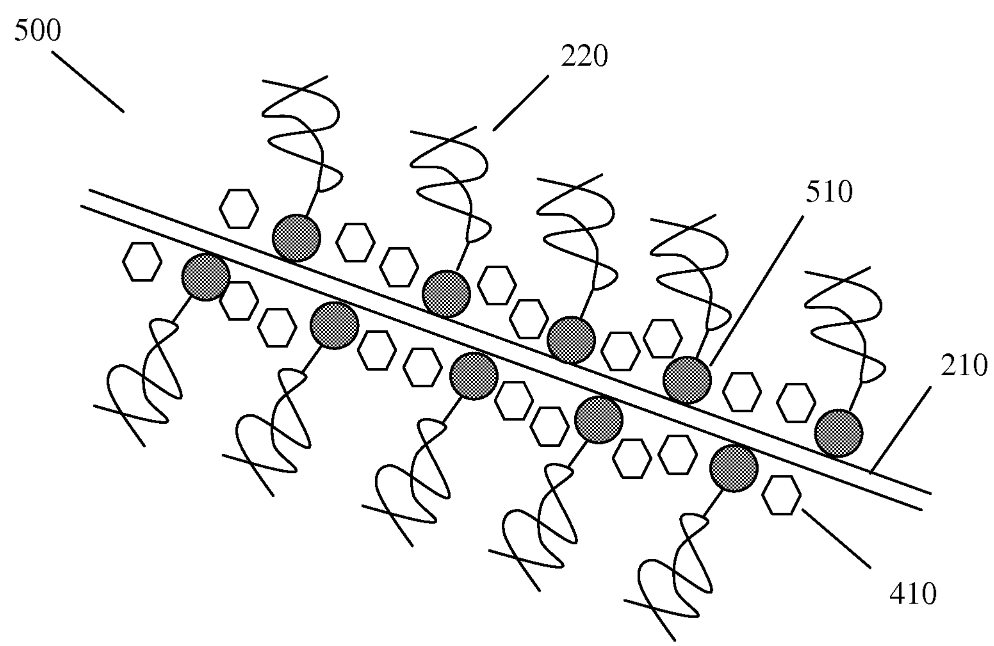
FIG. 5 is a schematic representation of a system for detecting the presence of a chemical or biological agent using an aptamer in accordance with an embodiment of the present invention.

The aptamers could be further stabilized through use of nanoparticles, as shown in system 500 in FIG. 4. The aptamers 220 are bound to the nanoparticle 510 using one of a number of chemical processes known in the art. Nanoparticles 510 can be formed from any suitable molecules, including but not limited to metals such as gold, silver, and platinum, and plastics. The nanoparticles can be bound to the textile fiber 210, and can be optionally combined with the stabilizer, such as trehalose molecules 410. Alternatively, nanoparticles could be deposited onto the textile fiber then the aptamers could be sandwiched between the first nanoparticle and a second, colored, nanoparticle.

At step 120 of the method depicted in FIG. 1, the textile comprising the anti-biological or chemical agent aptamer is exposed to an environment potentially comprising the target agent. For example, the textile can be clothing as small as a patch or button to as large as a full suit worn by anyone who might be exposed to harmful agents. This could include military personnel, emergency responders, haz-mat teams, firemen, policemen, and a wide variety of other individuals. At step 130 of the method the target agent binds to the aptamer.

Figure 6:
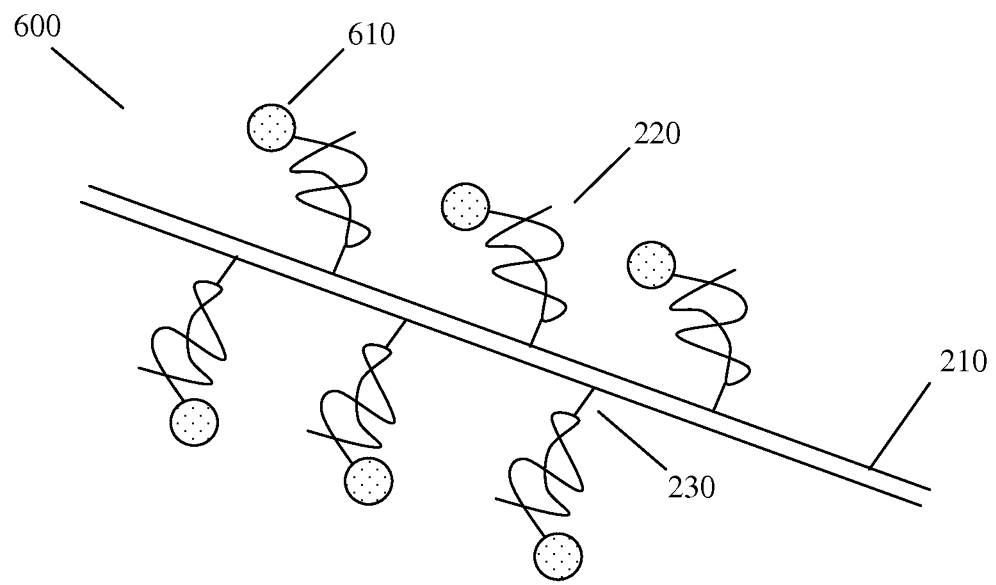
FIG. 6 is a schematic representation of an array for detecting the presence of a chemical or biological agent using an aptamer in accordance with an embodiment of the present invention.

At steps 140 and 150 of the method depicted in FIG. 1, the system detects and then reports the presence of the target agent. Accordingly, the textile/aptamer system also comprises a mechanism for notifying a user if a target chemical or biological agent is detected (i.e, bound by the aptamer). For example, the system can include a nanoparticle 610 bound to a terminal end of the aptamer 220, as shown in system 600 in FIG. 6, using any one of a number of chemical processes known in the art. Further, system 600 can be combined with any of the other elements described herein, including a stabilizer such as trehalose and a nanoparticle to bind the aptamer to the textile. According to one embodiment, nanoparticle 610 is a colored nanoparticle. There are a number of colored nanoparticles known in the art, including but not limited to nanoparticles used for electronic inks.

In yet another embodiment, a porous nanoparticles could also be used where the target chemical or biological agent must diffuse into the nanoparticle for the cleavage reaction to occur, again changing the color of the fiber and releasing a second colored nanoparticle attached through the oligonucleotide.

Figure 7:
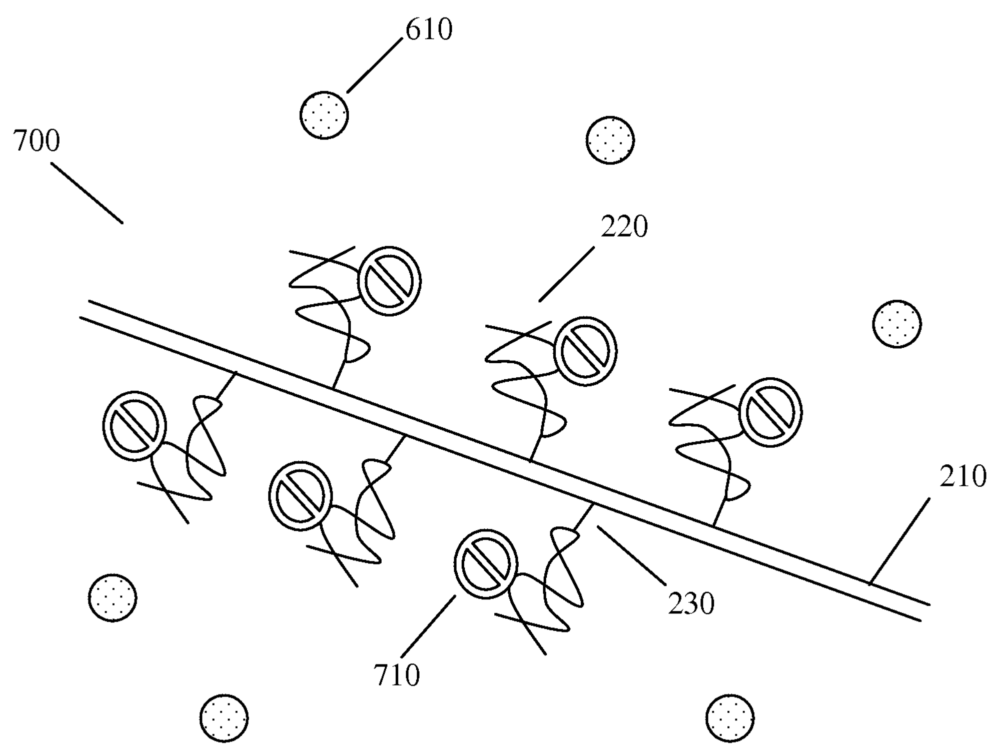
FIG. 7 is a schematic representation of an array for detecting the presence of a chemical or biological agent using an aptamer in accordance with an embodiment of the present invention.

For detection of the target chemical or biological agent 710, nanoparticle 610 would be released from the system as shown in FIG. 7, including being released from aptamer 220 as a consequence of target binding to the aptamer, or the terminal portion of aptamer 220 being cleaved from the system by binding of the target. This would result in a color change to the system. As perceived by the wearer or user, the textile would appear to change color in the presence of the target chemical or biological agent 710. In an alternative embodiment, detection mechanism 610 is a dye or color imparting agent that is activated, including by adding or imparting color to the textile fiber itself, upon release from the aptamer. For example, the dye or color imparting agent may react with the textile or components embedded within the textile to yield a color only when the agent is released from the aptamer or the system via binding of the chemical or biological agent of interest. In yet another embodiment, the detection mechanism 610 is a color quencher that quenches a color upon binding of the chemical or biological agent of interest. For example, the color quencher may react with the textile or components embedded within the textile to quench a color only when the agent is released from the aptamer or the system via binding of the chemical or biological agent of interest.

Figure 8:
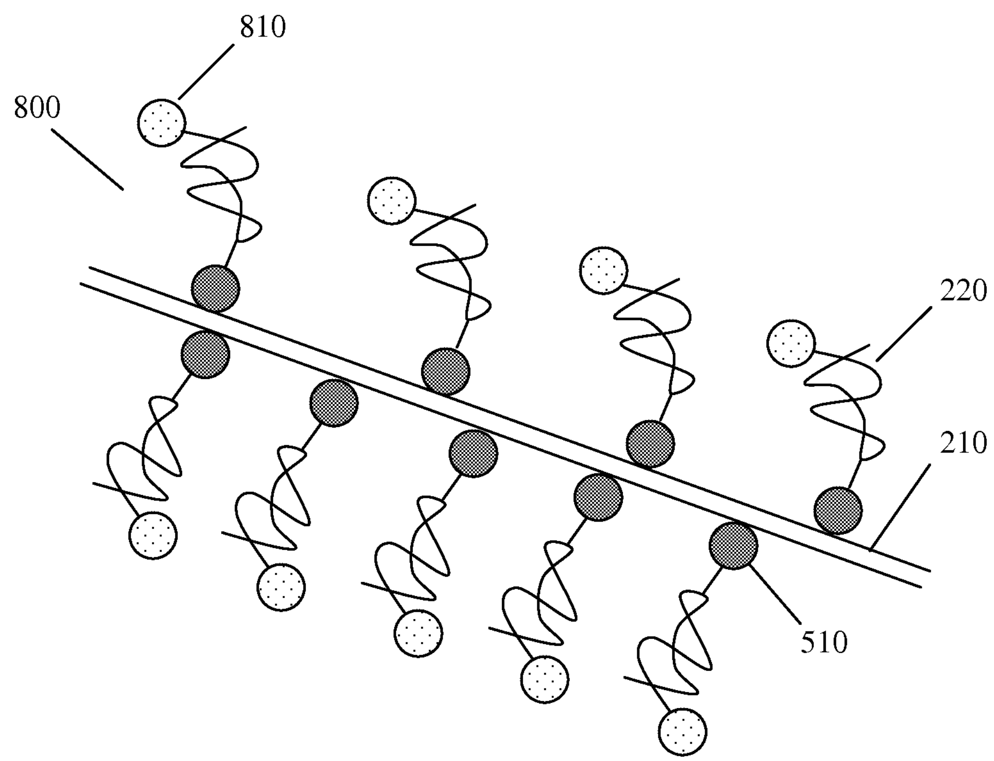
FIG. 8 is a schematic representation of an array for detecting the presence of a chemical or biological agent using an aptamer in accordance with an embodiment of the present invention.
Figure 9:
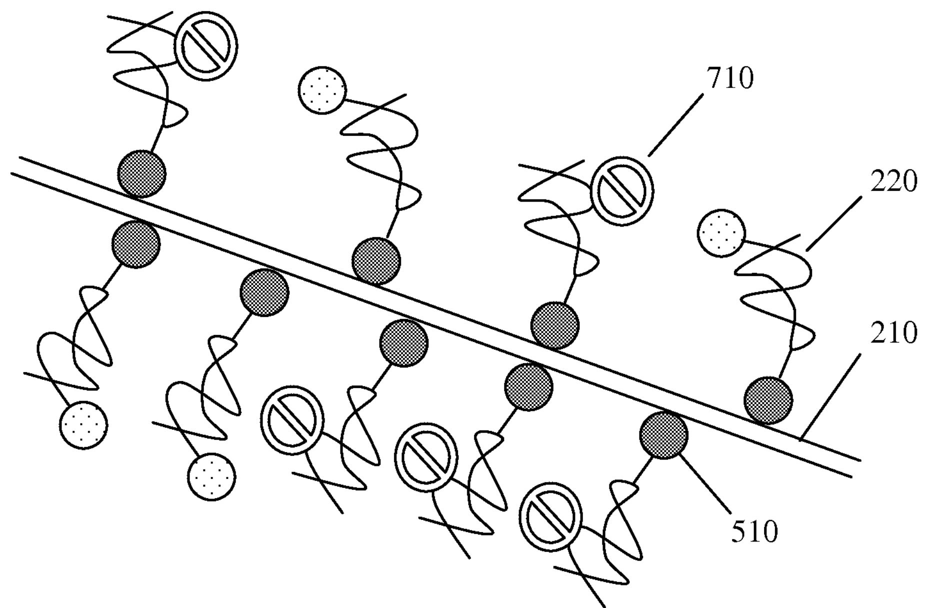
FIG. 9 is a schematic representation of an array for detecting the presence of a chemical or biological agent using an aptamer in accordance with an embodiment of the present invention.

Detection could also be achieved electrically, as shown in system 800 in FIG. 8. Nanoparticle 510 is a conductive metal nanoparticle such as gold, silver, platinum, or any one of a wide variety of conductive nanoparticles, and is attached to the textile fiber 210 using any one of a number of chemical processes known in the art. An insulating nanoparticle 810 is attached to the terminal end of aptamer 220 using any one of a number of chemical processes known in the art, increasing the resistance of the system. Upon binding of the chemical or biological target of interest 710, as shown in FIG. 9, insulating nanoparticle 810 leaves the system and the resistance of the overall system decreases, which could be measured by a monitoring circuit. When that decrease in resistance is detected by the monitoring circuit, a signal could be given to the user directly or could be sent wirelessly to a different location. System 800 could further be combined with any of the other elements described herein, including a stabilizer such as trehalose and a nanoparticle to bind the aptamer to the textile.

Although the present invention has been described in connection with a preferred embodiment, it should be understood that modifications, alterations, and additions can be made to the invention without departing from the scope of the invention as defined by the claims.

What is claimed is:

1. A method for detecting the presence of a biological or chemical target using a textile-based sensor, the method comprising the steps of:

contacting a sample with a sensor, the sensor comprising: (i) a textile comprising a plurality of textile fibers, wherein the textile is a textile patch; (ii) a plurality of aptamer molecules extending outwardly from at least some of the plurality of textile fibers of the textile, each aptamer molecule comprising a target binding domain selected to bind to the target when the target is present, and each aptamer molecule further comprising a metal nanoparticle reversibly immobilized to a first end of each of said plurality of aptamer molecules, wherein said metal nanoparticle is released from the aptamer molecule when the target binds to the target binding domain; and (iii) a stabilizing agent selected to stabilize the plurality of aptamer molecules, wherein the stabilizing agent is selected from the group consisting of trehalose, a natural polymer, a synthetic polymer, and combinations thereof, and further wherein the stabilizing agent comprises a plurality of stabilizing nanoparticles immobilized to the plurality of textile fibers, wherein each aptamer molecule is immobilized at a second end to at least one of the stabilizing nanoparticles; and detecting a reporter signal generated by the sensor in response to the target binding to the target binding domain of one or more of the plurality of aptamer molecules.

2. The method of claim 1, wherein the reporter signal notifies the user to the present presence of a biological or chemical target.

3. The method of claim 1, wherein the textile patch is positioned on a clothing item of a user in an environment where the biological or chemical target may be present.

4. The method of claim 1, wherein the stabilizing agent is a hydrogel.

5. The method of claim 1, wherein the metal nanoparticle is a conductive metal nanoparticle.

6. The method of claim 5, wherein the conductive metal nanoparticle is selected from the group consisting of gold, silver, platinum, and combinations thereof.

7. The method of claim 1, wherein release of one or more of the nanoparticles results in a change in an electrical characteristic of the sensor.

8. The method of claim 7, further comprising the step of monitoring the sensor for the change in the electrical characteristic of the sensor.

9. The method of claim 7, further comprising the step of transmitting a detected reporter signal.

10. The method of claim 9, wherein said detected reporter signal is transmitted wirelessly to a location remote from the sensor.

11. The method of claim 1, wherein the reporter signal is a color change.

12. The method of claim 11, wherein the color change results in a color modification of at least a portion of the textile.

13. The method of claim 1, wherein the reporter signal is a dyeing of one or more of the plurality of textile fibers.

14. The method of claim 1, wherein the reporter signal comprises a quenching of a color.

* * * * *